US009606206B2

United States Patent
Boernert et al.

(10) Patent No.: US 9,606,206 B2
(45) Date of Patent: Mar. 28, 2017

(54) RADIATION THERAPY SYSTEM WITH REAL TIME MAGNETIC RESONANCE MONITORING

(75) Inventors: Peter Boernert, Hamburg (DE); Johannes Adrianus Overweg, Hamburg (DE)

(73) Assignee: KONINKLIJKE PHILIPS ELECTRONICS N.V., Eindhoven (NL)

( * ) Notice: Subject to any disclaimer, the term of this patent is extended or adjusted under 35 U.S.C. 154(b) by 1203 days.

(21) Appl. No.: 12/997,020

(22) PCT Filed: Jun. 16, 2009

(86) PCT No.: PCT/IB2009/052550
§ 371 (c)(1),
(2), (4) Date: Dec. 9, 2010

(87) PCT Pub. No.: WO2009/156896
PCT Pub. Date: Dec. 30, 2009

(65) Prior Publication Data
US 2011/0087090 A1    Apr. 14, 2011

(30) Foreign Application Priority Data

Jun. 25, 2008  (EP) .................................... 08158941

(51) Int. Cl.
*A61B 5/05*  (2006.01)
*G01R 33/48*  (2006.01)
(Continued)

(52) U.S. Cl.
CPC .......... *G01R 33/4808* (2013.01); *A61B 5/055* (2013.01); *A61N 5/1049* (2013.01);
(Continued)

(58) Field of Classification Search
CPC ........... G07D 11/0012; G07D 11/0018; G07D 11/0081; A61B 5/055; A61N 2005/1055
(Continued)

(56) References Cited

U.S. PATENT DOCUMENTS

| 5,378,986 A * | 1/1995 | Seo et al. ...................... 324/309 |
| 2001/0001807 A1 | 5/2001 | Green |

(Continued)

FOREIGN PATENT DOCUMENTS

| WO | 03099380 A1 | 12/2003 |
| WO | 2004024235 A1 | 3/2004 |
| WO | 2007045076 A1 | 4/2007 |

OTHER PUBLICATIONS

What is ionizing radiation? Armed forces Radiobiology Research Institute http://www.usuhs.edu/afrri/outreach/ionizing.htm, May 4, 2009.*

(Continued)

*Primary Examiner* — James Kish (57) ABSTRACT

A radiation therapy system comprises: a radiation therapy subsystem (20, 22, 32) configured to perform radiation therapy by applying radiation pulses to a region of a subject at pulse intervals (Tpi); a magnetic resonance (MR) imaging subsystem (10, 16, 30, 36) configured to acquire a dataset of MR imaging data samples from the region of the subject over one or more MR sampling intervals (TAQ) that are longer than the pulse intervals, the one or more MR sampling intervals overlapping at least some of the pulse intervals; a synchronizer (40) configured to identify MR imaging data samples of the dataset whose acquisition times overlap pulse intervals; and a reconstruction processor (44) configured to reconstruct the dataset without the measured values for the MR imaging data samples identified as having acquisition times overlapping pulse intervals to generate a reconstructed MR image.

17 Claims, 3 Drawing Sheets

(51) Int. Cl.
    *A61B 5/055*     (2006.01)
    *G01R 33/56*     (2006.01)
    *A61N 5/10*     (2006.01)
    *G01R 33/561*     (2006.01)

(52) U.S. Cl.
    CPC ............ *G01R 33/56* (2013.01); *A61N 5/1038* (2013.01); *A61N 5/1067* (2013.01); *A61N 2005/1055* (2013.01); *G01R 33/5608* (2013.01); *G01R 33/5611* (2013.01)

(58) Field of Classification Search
    USPC .......................................................... 600/411
    See application file for complete search history.

(56) References Cited

U.S. PATENT DOCUMENTS

| 2001/0049474 | A1  | 12/2001 | Wagshul |         |
|---|---|---|---|---|
| 2005/0197564 | A1* | 9/2005  | Dempsey | 600/411 |
| 2008/0021304 | A1  | 1/2008  | Stemmer |         |
| 2009/0149735 | A1* | 6/2009  | Fallone et al. | 600/411 |

OTHER PUBLICATIONS

Candes et al: "Robust Uncertainty Principles: Exact Signal Reconstruction From Highly Incomplete Frequency Information"; IEEE Transactions on Information Theory, Feb. 2006, vol. 52, No. 2, pp. 489-509.

Donoho, D.: "Compressed Sensing"; IEEE Transactions on Information Theory, Apr. 2006, vol. 52, No. 4, pp. 1289-1306.

Griswold et al: "Generalized Autocalibrating Partially Parallel Acquisitions (GRAPPA)"; Magnetic Resonance in Medicine, 2002, vol. 47, pp. 1202-1210.

Pruessmann et al: "SENSE: Sensitivity Encoding for Fast MRI"; Magnetic Resonance in Medicine, 1999, vol. 42, pp. 952-962.

Sodickson et al: "Simultaneous Acquisition of Spatial Harmonics (SMASH): Fast Imaging With Radiofrequency Coil Arrays"; MRM, 1997, vol. 38, pp. 591-603.

Atkinson et al "Coil-Based Artifact Reduction" Magnetic Resonance in Medicine 52 (2004) p. 825-830.

Feinberg et al "Halving MR Imaging Time by Conjugation: Demonstration at 3.5Kg1" Radiology vol. 161 No. 2, p. 527-531.

* cited by examiner

RADIATION THERAPY SYSTEM WITH REAL TIME MAGNETIC RESONANCE MONITORING

FIELD OF THE INVENTION

The following relates to the medical arts, imaging arts, magnetic resonance arts, and related arts. It finds particular application in radiation therapy and is described with particular reference thereto.

BACKGROUND OF THE INVENTION

In radiation therapy, spatially targeted dosages of ionizing radiation are applied to a tumor or other region containing cancerous or malignant tissue. Growing and rapidly multiplying cancer cells are often more susceptible to damage from ionizing radiation as compared with normal cells, and so enforced by the higher dosage administered by proper planning, the applied radiation preferentially kills cancerous or malignant tissue. Nonetheless, ionizing radiation is harmful to both malignant and healthy cells, and so precise spatial targeting of the radiation is important for limiting collateral damage to healthy tissue. Damage to healthy tissue is also typically controlled by performing the radiation therapy in a series of sessions extending over several days, weeks or months, with the expectation that radiation damage to healthy tissue may undergo healing during the time intervals between treatment sessions.

In radiation therapy, the radiation beam is applied at angular positions around the subject in a manner that combines to produce a targeted total radiation dosage spatial distribution that is concentrated on the tumor or other region to be treated. Angular coverage can be achieved by using several stationary radiation sources distributed around the subject, or by revolving a radiation source such as a linear accelerator (linac) around the subject (i.e., tomotherapy). The radiation therapy is planned in advance for a specific subject, based on imaging data for that subject acquired using computed tomography (CT), magnetic resonance (MR) imaging, or another suitable imaging modality. To achieve sufficiently accurate radiation targeting, the planning is performed using images acquired for the specific subject to undergo therapy. The tumor or other target is delineated in the images, along with delineation of critical organs or regions where radiation dosage must be limited. Computer simulations or other electronic calculations are used to optimize the spatial profiles and intensities of the radiation beam to concentrate the radiation in the target while minimizing exposure of critical but possibly normal organs or regions.

In most existing radiation therapy facilities, the CT, MR, or other imaging system used for the planning is physically separate from the radiation therapy system that includes the ionizing radiation source or sources. The spatial frame of reference of the imaging must then be registered with the spatial frame of reference of the radiation therapy system, for example using indicator markers glued to the subject. Registration errors result in less well targeted radiation therapy, which can reduce its effectiveness at combating the cancer and can increase collateral damage to healthy tissue. Another problem is that the time between planning data acquisition and radiation treatment can be many days or even longer. In the interim, patient anatomy may shift or change due to bladder filling, bowel motion, weight loss or gain, or so forth.

Still further, although the subject is generally immobilized during the radiation therapy treatment, various kinds of subject motion can still occur during the radiation therapy, such as respiration, bulk subject motion, or so forth.

In view of these issues, it has been recognized that it would be advantageous to image the subject using an imaging modality physically connected with the radiation therapy system. Various such "hybrid" systems have been proposed, which combine a CT or MR system with a radiation treatment system. In some MR imaging-based arrangements, the MR scanner magnet is divided into two halves defining an axial gap that receives the radiation therapy system or that allows the radiation therapy beam to pass (see, e.g. Demsey, U.S. Publ. Appl. No. 2005/0197564 A1; Green, U.S. Publ. Appl. No. 2001/0001807 A1; Fallone et al., WO 2007/045076 A1; Lagendijk et al, WO 2004/024235 A1). Other MR scanner components, such as gradient coils and radio frequency coils, can be similarly divided or arranged to lie outside of the gap, or can be made sufficiently thin or of suitable materials such that the therapy beam can pass through the components without substantial attenuation. In such a system, both the imaging and the radiation therapy modalities share the same system of coordinates, which removes or simplifies the registration component of the radiation therapy planning process. Additionally, radiation therapy planning can be performed immediately before each radiation therapy session, thus minimizing error due to changes in patient anatomy between the planning and therapy.

To address possible subject movement during the radiation therapy session, it has been contemplated to use such a hybrid system to perform imaging during the radiation therapy session, so as to detect subject motion. However, difficulties arise in performing concurrent imaging and radiation therapy. Computed tomography (CT) scanners are not well suited for such concurrent operation, because it is difficult or impossible to physically arrange for the x-ray beam of the CT scanner to simultaneously probe the spatial region undergoing radiation therapy. MR has been recognized as a better imaging modality candidate for concurrent imaging. However, interference caused by the radiation therapy system has heretofore been found to prevent acquisition of quality MR images during the radiation therapy.

Fallone et al., WO2007045076 has proposed to interleave MR imaging and radiation therapy operations by preventing linear accelerator (linac) pulsing during the MR acquisition window. This means that radiation therapy is not performed during the imaging. Even for rapid real-time three-dimensional imaging sequences, the number of imaging data sampling intervals is sufficiently large that the duty cycle of the radiation source under this approach is substantially extended, thus prolonging the therapy session.

The following provides new and improved apparatuses and methods which overcome the above-referenced problems and others.

SUMMARY OF THE INVENTION

In accordance with one disclosed aspect, a radiation therapy method is disclosed, comprising: performing radiation therapy by applying radiation pulses to a region of a subject during pulse intervals; acquiring a dataset of magnetic resonance (MR) imaging data samples from the region of the subject over one or more MR sampling intervals that are longer than the pulse intervals, the one or more MR sampling intervals overlapping at least some of the pulse intervals; and reconstructing the dataset, without those measured MR imaging data samples acquired during acquisition times that overlap pulse intervals, to generate a reconstructed MR image.

In accordance with another disclosed aspect, a radiation therapy system is disclosed, comprising: a radiation therapy subsystem configured to perform radiation therapy by applying radiation pulses to a region of a subject at pulse intervals; a magnetic resonance (MR) imaging subsystem configured to acquire a dataset of MR imaging data samples from the region of the subject over one or more MR sampling intervals that are longer than the pulse intervals, the one or more MR sampling intervals overlapping at least some of the pulse intervals; a synchronizer configured to identify MR imaging data samples of the data set whose acquisition times overlap pulse intervals; and a reconstruction processor configured to reconstruct the dataset, without the measured values for the MR imaging data samples identified as having acquisition times overlapping pulse intervals, to generate a reconstructed MR image.

One advantage resides in providing for shorter radiation therapy sessions.

Another advantage resides in providing real-time monitoring for radiation therapy.

Another advantage resides in providing real-time adaptive radiation therapy.

Still further advantages will be apparent to those of ordinary skill in the art upon reading and understanding the following detailed description.

DETAILED DESCRIPTION OF EMBODIMENTS

Figure 1:
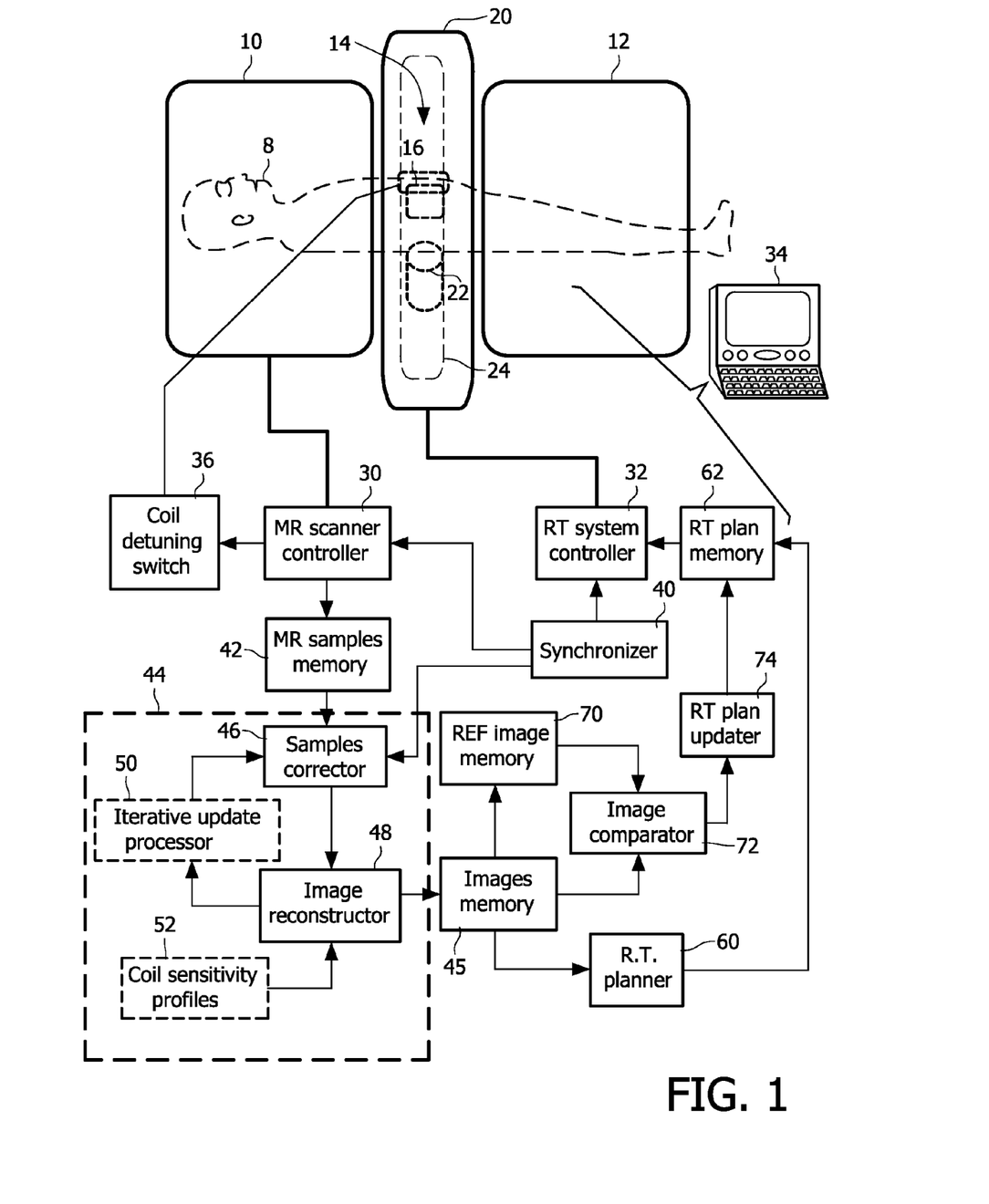
FIG. 1 diagrammatically shows a hybrid system integrating a radiation therapy system with a magnetic resonance (MR) scanner, and further including components configured to enable concurrent radiation therapy and MR imaging.

With reference to FIG. 1, a hybrid system receives a subject 8 (shown in phantom) for radiation therapy. The illustrated subject 8 is a human subject, but embodiments constructed to provide radiation therapy for animal subjects are also contemplated. The hybrid system includes a magnetic resonance (MR) scanner having a magnet formed of two magnet portions 10, 12 configured to have an annular gap 14 therebetween. The MR scanner includes other components such as magnetic field gradient coils (not shown, typically disposed within the magnet 10, 12) and one or more radio frequency coils such as a representative one or more local radio frequency coils 16 (shown in phantom).

A radiation therapy system includes a housing or other support or body 20 supporting a radiation source, such as a diagrammatically indicated linear accelerator (linac) 22 (shown in phantom) arranged to move or revolve around the subject 8 along a circumferential gantry or track 24 (shown in phantom) to enable irradiation of the subject 8 from anywhere along a 360° circumference. Instead of the illustrated tomographic linac arrangement 22, 24, the radiation therapy system can comprise a plurality of stationary radiation sources disposed at fixed positions around the subject 8 to enable simultaneous irradiation from multiple (fixed) angular positions.

Any components of the MR system that are disposed in a line-of-sight between the radiation source 22 (or, more generally, the circumferential path 24 of radiation source revolution) and the subject 8 are suitably made of a material or materials, or are sufficiently thin, to enable radiation generated by the radiation source 22 to pass through such MR components and into the subject 8 without substantial attenuation in the MR components. For example, the one or more radio frequency coils 16 can be made of thin copper striplines mounted on a radiation-transmissive board and surrounded by an optional radiation-transmissive housing (sub-components not shown). Alternatively, if an MR component spans a small angular viewing range of the radiation source, such an MR component can be positioned at a location corresponding to an angular position or span over which the radiation source 22 is not pulsed to emit therapy radiation. It should be noted that although the illustrated MR system includes two separated magnet portions 10, 12 providing the annular gap 14 for passage of therapy radiation, it is also contemplated for the MR magnet to be continuous across the region of the gap 14 but to be made sufficiently thin in this region, and/or of sufficiently radiation-transmissive material, so as to pass the therapy radiation without substantial attenuation.

The hybrid system further includes suitable control electronics, such as an MR scanner controller 30 configured to control the MR scanner subsystem to acquire MR imaging data, a radiation therapy system controller 32 configured to control the radiation therapy subsystem to perform radiation therapy by applying radiation pulses to a region of a subject 8 during pulse intervals that are separated by pulse repetition intervals, and a computer 34 or other user interface communicating with the controllers 30, 32 to enable a radiologist or other user to operate the MR scanner and radiation therapy subsystems. Although illustrated as separate components, in some embodiments it is contemplated for one or both controllers 30, 32 to be embodied by the computer 34 executing suitable control software. The electronics illustrated as examples in FIG. 1 further include a control detuning switch 36 coupled with the one or more radio frequency coils 16 to detune the coil during radio frequency excitation. In embodiments employing the detuning switch 36, the radio frequency coil or coils 16 is used as a receive-only coil, and another radio frequency coil such as a whole-body coil (not shown) is used for the radio frequency excitation. Although the detuning switch 36 is illustrated in FIG. 1 as a separate component, it is contemplated for the detuning switch 36 or portions thereof to be integrated into one or both of the MR scanner controller 30 and/or the radio frequency coil or coils 16.

The illustrated hybrid system is an example. Other hybrid systems having a geometry enabling an MR scanner to image a subject positioned for radiation therapy treatment are also contemplated. As another example, if the radiation therapy system employs a plurality of stationary radiation sources, then the MR scanner magnet can comprise a continuous cylinder with a plurality of fixed-position openings for passing therapy radiation generated by the stationary radiation sources.

To operate the MR imaging while simultaneously applying therapeutic radiation pulses so as to implement radiation therapy with real-time monitoring by MR imaging, the impact of the radiation pulses applied by the radiation source 22 on the MR imaging data is considered herein.

Figure 2:
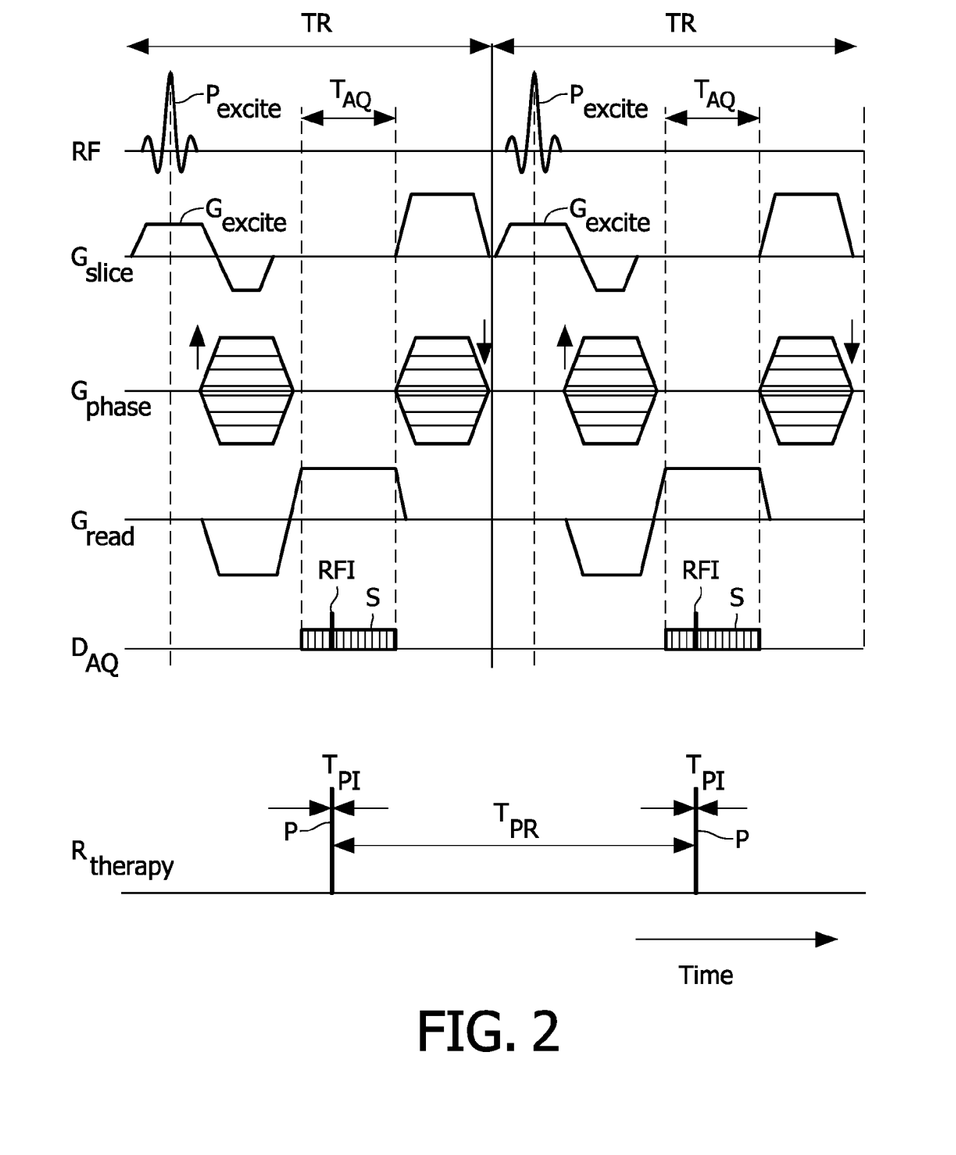
FIG. 2 diagrammatically shows an MR gradient echo pulse sequence suitable for acquiring one line of k-space, along with pulses of a radiation therapy beam.

With brief reference to FIG. 2, the radiation source 22 applies a pulsed beam of ionizing radiation, such as high energy gamma particles (i.e., gamma photons), or alpha particles, or beta particles, or protons, or x-ray photons, or so forth, directed into the region of the subject 8 containing the tumor or other malignancy undergoing treatment. The ionizing radiation interacts with and damages the tumor tissue. The interaction of the ionizing radiation with tissue also generates a shower of secondary electrons which further contribute to tissue damage. This burst of secondary electrons emits a pulse of radio frequency noise that causes radio frequency interference affecting the sensitive receive system of the MR scanner. The radio frequency interference degrades the MR imaging data acquired during the pulse interval, thus degrading the quality of the reconstructed MR image. FIG. 2 diagrammatically shows output timing for a typical linac at the bottommost trace labeled "$R_{therapy}$". The linac outputs gamma rays in a pulsed mode in which each gamma beam pulse P has a pulse duration or pulse interval $T_{PI}$ that is typically of order 10 microseconds although longer or shorter pulse intervals are also contemplated, and the pulses repeated at a pulse repetition interval $T_{PR}$ that is typically of order 0.1-10 milliseconds although longer or shorter pulse repetition intervals are also contemplated The pulses P are diagrammatically shown in FIG. 2 as square pulses, but in general the pulses P can have various shapes. In some embodiments, each pulse P includes a high-frequency modulation having a frequency on the order of 1 GHz although higher or lower modulation frequencies, or no such modulation, are also contemplated. This frequency is well above the MR frequency range and is not expected to produce substantial interference with the MR imaging.

FIG. 2 also shows a typical MR gradient echo sequence of a type sometimes used for imaging. Although a gradient echo sequence is illustrated and described as an example, it is to be appreciated that the MR imaging can employ substantially any type of imaging sequence, such as an echo-planar imaging (EPI) sequence, a turbo spin echo (TSE) sequence, or so forth. In FIG. 2, the illustrative gradient echo sequence is diagrammed by plotting versus time: applied radio frequency pulses (trace labeled "RF"); the slice-select magnetic field gradient (trace labeled "$G_{slice}$"); the phase-selective magnetic field gradient (trace labeled "$G_{phase}$"); the readout magnetic field gradient (trace labeled "$G_{read}$"); and data acquisition intervals (trace labeled "$D_{AQ}$"). The illustrative gradient echo sequence employs a slice-selective radio frequency excitation comprising a radio frequency pulse $P_{excite}$ and a simultaneously applied slice-selective magnetic field gradient $G_{excite}$. This excitation $P_{excite}$, $G_{excite}$ is followed by in-slice phase- and readout-encoding magnetic field gradients (diagrammed on the "$G_{phase}$" and "$G_{read}$" traces but not labeled in FIG. 2). MR imaging data samples S are acquired from the region of the subject 8 over an MR sampling interval $T_{AQ}$. The MR sampling acquires an entire line of k-space comprising, for example, 256 samples, over the MR sampling interval $T_{AQ}$. That is, MR imaging data samples S comprise one line of k-space, such as 256 samples in some embodiments. The entire pulse sequence including the excitation $P_{excite}$, $G_{excite}$, acquisition of samples S, and associated magnetic field gradients occupies a repetition time interval TR, and this gradient echo sequence is repeated to acquire each line of k-space until a full dataset, of for example 256×256 samples, is acquired. FIG. 2 diagrams two repetitions of the gradient echo sequence (i.e., time interval 2×TR).

To provide a non-limiting quantitative example, TR may be of order 3-4 milliseconds, and $T_{AQ}$ may be of order 1 millisecond (1000 microseconds). If 256 k-space samples are acquired over $T_{AQ}$, then each MR imaging data sample is acquired over about 4 microseconds. These are merely illustrative values, and other samplings and time intervals may be used. As already noted, a single therapeutic radiation pulse P typically occupies a pulse interval $T_{PI}$ of about 10 microseconds, which corresponds to approximately 3 MR imaging data samples for the above illustrative numerical example.

As indicated in FIG. 2, the therapeutic radiation pulse P generates radio frequency interference RFI over the pulse interval $T_{PI}$. This radio frequency interference typically appears as a large peak or spike in the acquired MR imaging data. As a result, those MR imaging data samples whose acquisition times overlap pulse intervals $T_{PI}$ are corrupted. Reconstructing the dataset including these corrupted MR imaging data samples can be expected to produce images with substantial artifacts.

It is recognized herein, however, that only those MR imaging data samples whose acquisition times overlap pulse intervals $T_{PI}$ are corrupted. MR imaging data samples whose acquisition times do not overlap pulse intervals $T_{PI}$ are not corrupted, and are usable data. Since the pulse repetition interval $T_{PR}$ is of order 0.1-10 milliseconds, and the MR sampling interval $T_{AQ}$ for the illustrative numerical example is of order 1 millisecond, for the illustrative numerical example there are generally fewer than 10 pulse intervals $T_{PI}$ overlapping the MR sampling interval $T_{AQ}$, and possibly as few as one or no overlapping pulse intervals $T_{PI}$. It follows that between about 88% and 100% of the MR imaging data samples acquired over the interval MR sampling interval $T_{AQ}$ are usable data, even when the radiation therapy is performed simultaneously with the MR imaging data acquisition.

With returning reference to FIG. 1, the hybrid system further includes a synchronizer 40 configured to identify MR imaging data samples of the imaging dataset whose acquisition times overlap pulse intervals. In some embodiments the synchronizer 40 is further configured to select at least one of (i) the repetition time TR of the dataset acquisition (e.g., the gradient echo sequence in the illustrative example of FIG. 2) and (ii) the pulse repetition time interval $T_{PR}$ separating the pulse intervals $T_{PI}$ in order to define which MR imaging data samples of the dataset have acquisition times overlapping pulse intervals. The MR imaging data samples are stored in a MR samples memory 42. A reconstruction processor 44 is configured to reconstruct the dataset without measured values for the MR imaging data samples identified by the synchronizer 40 as having acquisition times overlapping pulse intervals to generate a reconstructed MR image. The reconstructed image is suitably stored in an images memory 45.

Inclusion of measured values for the MR imaging data samples identified by the synchronizer 40 as having acquisition times overlapping pulse intervals can be avoided by including a samples corrector 46 that replaces corrupted data samples by estimated ones for those MR imaging data samples, and an image reconstructor 48 that reconstructs the dataset including the inserted non-measured or estimated values. The inserted non-measured or estimated values can be zero padding values, or average values obtained by averaging the measured values of neighboring MR imaging data samples, or can be otherwise generated or estimated.

In some embodiments an iterative reconstruction process is employed. The samples corrector 46 inserts initial non-measured or estimated MR imaging data sample values computed as zero padding values or neighbor-averaged values. The image reconstructor 48 reconstructs this initial dataset to form an initial reconstructed image. An iterative update processor 50 then computes and inserts updated non-measured or estimated values for those MR imaging data samples identified by the synchronizer 40 as having acquisition times overlapping pulse intervals $T_{PI}$. The update processor 50 can compute the updated non-measured or estimated values, for example, by performing spatial filtering of the reconstructed image and generating a simulated dataset of MR imaging data samples from the reconstructed and filtered MR image and updating the non-measured or estimated MR imaging data sample values based on the generated simulated dataset. The simulation employs an "inverse" image reconstruction process that comports with the spatial encoding used in acquiring the MR imaging data samples, such as a Fourier transform, a back-projection or a gridding algorithm. The image reconstructor 48 then reconstructs the dataset with the updated inserted non-measured or estimated MR imaging data sample values to generate an improved reconstructed MR image. This process can be iterated zero or more times to iteratively improve the non-measured or estimated MR imaging data sample values and thereby iteratively improve the overall reconstructed image.

In another approach, inclusion of measured values for the MR imaging data samples identified by the synchronizer 40 as having acquisition times overlapping pulse intervals can be avoided by omitting those MR imaging data samples, such that the dataset is undersampled, and compensating for the undersampling in the reconstruction based on additional information provided by a plurality of radio frequency receive coils having different coil sensitivities. This approach is similar to the SENSE, SMASH or GRAPPA technique (See, e.g., Pruessmann et al. MRM vol. 42 pages 952-62 (1999); Sodickson et al. MRM vol. 38 pages 591-603 (1997); Griswold et al. MRM vol. 47 pages 1202-10 (2002)). Here, the one or more radio frequency coils 16 comprise a plurality of radio frequency receive coils having different coil sensitivities. For example, the radio frequency coils 16 can be a phased or SENSE coil array. Coil sensitivity profiles 52 are generated for the coils of the plurality of radio frequency receive coils using suitable calibration pulse sequences in the same way coil sensitivity profiles are generated for use in SENSE imaging. The image reconstruction processor 48 then performs the reconstruction compensating for the undersampling based on the additional information contained in the coil sensitivity profiles 52.

With continuing reference to FIG. 1, the MR subsystem including the reconstruction processor 44 performs real-time magnetic resonance monitoring of the radiation therapy process performed by the radiation therapy subsystem. By "real-time" monitoring, it is meant that the MR imaging data acquisition is performed concurrently with the radiation therapy such that pulse intervals $T_{PI}$ overlap the MR imaging sequence and occasionally overlap MR sampling intervals $T_{AQ}$, which are longer than the pulse intervals $T_{PI}$. The synchronizer 40 operatively couples the MR and radiation therapy subsystems by identifying, and in some embodiments controlling, which MR imaging data samples have acquisition times that overlap pulse intervals $T_{PI}$. The reconstruction processor 44 inserts non-measured/estimated values for those MR imaging data samples identified as having acquisition times overlapping pulse intervals, or omits those MR imaging data samples that have acquisition times overlapping pulse intervals $T_{PI}$, and accordingly is able to reconstruct an accurate MR image in spite of data corruption due to RFI caused by the therapeutic radiation pulses.

In some embodiments, the synchronizer 40 is operatively coupled with the MR scanner controller 30 so as to identify to the MR scanner controller 30 when a therapeutic radiation pulse will occur. In such embodiments, the MR scanner controller 30 optionally performs an operation such as causing the coil detuning switch 36 to detune the one or more radio frequency coils 16 during the corresponding pulse interval $T_{PI}$. Such detuning can reduce the magnitude of the therapeutic pulse-induced RFI received by the coil or coils 16. If the RFI intensity is high enough, such detuning may also be beneficial in preventing overloading of the receive coil or coils 16 by the RFI and damage to the coil or coils 16 possibly caused by such overloading.

On the other hand, if the radio frequency coil or coils 16 are unlikely to be damaged by the RFI, then it is contemplated to omit coupling between the synchronizer 40 and the MR scanner controller 30, and to acquire measured values in the usual manner for those MR imaging data samples identified as having acquisition times overlapping pulse intervals. Such measured values are then replaced by the samples corrector 46 or omitted from the (undersampled) dataset used in image reconstruction, and so the actually measured values are not relevant to the image reconstruction.

The MR monitoring can be used to enhance the radiation therapy in various ways. In one contemplated radiation therapy session workflow, the MR subsystem is initially applied prior to applying radiation pulses in order to acquire one or more reference images that are used by a radiation therapy planner 60 to generate a radiation therapy plan that is stored in a radiation therapy plans memory 62. The radiation therapy planner 60 can employ substantially any type of radiation therapy planning software or algorithm suitable for planning tomographic or intensity-modulated radiation therapy. In a typical approach, the reference MR image or images are displayed on the user interface 34, and a radiologist or other user employs a pointing device to define: (i) a lasso or other delineation of the tumor or other region containing the malignancy; and (ii) a lasso or other delineation of any critical organs or regions whose radiation exposure is to be limited. The user specifies constraints such as the radiation dosage to be delivered in the region of the malignancy, maximum radiation dosage limits for the critical organs or regions, time limits for the radiation therapy session, and so forth. Based on a priori known radiation absorption characteristics of the various tissues of the subject identified in the reference image or images, the software simulates the radiation exposure profile for an initial radiation beam intensity, optional beam profile, and tomographic pattern. Parameters such as beam intensity (or beamlets intensity in the case of a modulated beam profile), tomographic pattern, and so forth are iteratively optimized until the simulated radiation exposure profile satisfies the constraints specified by the user. Suitable radiation therapy planning software is available, for example, from Philips Medical Systems, Eindhoven, The Netherlands.

The reference image or images used for the radiation planning are also optionally stored in a reference images memory 70. The radiation therapy subsystem executes the radiation therapy plan stored in the radiation therapy plan memory 62. The MR subsystem acquires MR images during execution of the radiation therapy plan so as to provide real-time monitoring of the subject 8 during the radiation therapy. These real-time monitoring MR images have high image quality due to the corrective action performed by the reconstruction processor 44 in replacing or omitting those MR imaging data samples whose acquisition times overlap pulse intervals. The real-time monitoring images are compared with the reference image or images stored in the reference images memory 70 by an image comparator 72 so as to identify any changes in the subject that have occurred since the radiation therapy planning stage. Such changes may include, for example, movement, respiration effects, changes in distribution of fluids in the subject, or so forth.

The information output by the image comparator 72 can be used in various ways. In some embodiments, the user interface 34 provides an audible and/or visually perceptible alarm to the radiologist or other user in the event that the monitoring images indicate that the subject has moved or otherwise changed in a significant way. The radiologist or other user is then expected to take action as appropriate, for example by repositioning the subject 8, updating the radiation therapy plan, or so forth.

In some embodiments, it is contemplated to employ the information output by the image comparator 72 to implement automated adaptive radiation therapy. In these embodiments, a radiation therapy plan updater 74 receives the information output by the image comparator 72 and makes any appropriate updates to the radiation therapy plan stored in the radiation therapy plan memory 62. The updated radiation therapy plan adjusts the subsequently applied radiation pulses to adapt the radiation therapy plan to accommodate the identified subject motion. For example, McNutt et al., WO 2003/099380 discloses some iterative approaches suitable for updating the radiation therapy plan to rapidly accommodate small or incremental subject changes, and can rapidly adapt beam intensity modulated radiation therapy plans including with large numbers of parameters. This is merely an example, and other radiation therapy plan updating algorithms can also be employed by the radiation therapy plan updater 74.

It is to be appreciated that the various processing and storage components 30, 32, 40, 42, 44, 45, 60, 62, 70, 72, 74 which are separately illustrated in FIG. 1 can be physically implemented in various combinations. For example, in some embodiments the storage components 42, 45, 62, 70 are implemented as storage of the computer 34, such as one or more of an internal hard drive, an optical disk, random access memory (RAM), read-only memory (ROM), or so forth. Alternatively, some or all of the storage components 42, 45, 62, 70 may be implemented as remote storage located at a remote Internet server, remote hospital network server, or so forth. Similarly, various of the processing components 30, 32, 40, 44, 60, 72, 74 may be variously embodied by the processor of the computer 34 executing suitable software, or by a remote Internet or hospital server executing suitable software, or by a hardware pipeline implementing a hard-coded algorithm and/or including ASIC components, or so forth.

In some embodiments, the synchronizer 40 identifies MR imaging data samples of the dataset whose acquisition times overlap therapeutic pulse intervals, but does not attempt to control these overlaps. In other embodiments, the synchronizer 40 selects at least one of (i) the MR sequence repetition time TR and (ii) the therapeutic pulse repetition time interval $T_{PR}$ separating the pulse intervals, in order to define or control which MR imaging data samples of the dataset have acquisition times overlapping pulse intervals. It is also contemplated to adjust or change the $T_{PR}$ value over the course of the MR scanning.

Figure 3A:
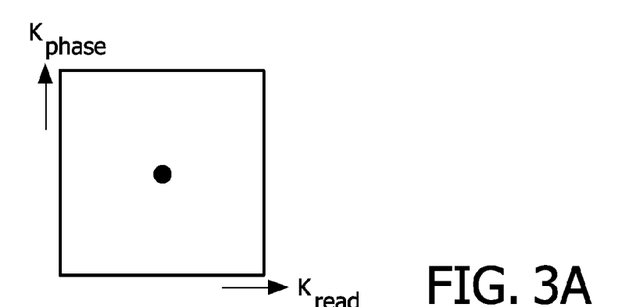
FIG. 3A diagrammatically shows sampling of a two dimensional slice of k-space, while FIGS. 3B, 3C, 3D, and 3E diagrammatically show sampling of the two-dimensional slice of k-space of FIG. 3A with holes in the sampling caused by pulsing of the radiation source of the radiation therapy system.

With reference again to FIG. 2 and with further reference to FIGS. 3A-3E, some illustrative synchronization schemes are set forth in which the synchronizer 40 controls or defines which MR imaging data samples of the dataset have acquisition times overlapping pulse intervals in a manner that facilitates reconstructing the dataset without measured MR imaging data samples for these MR imaging data samples. FIG. 3A illustrates the k-space for a slice acquired by gradient echo sequence of FIG. 2 without any therapeutic radiation pulses applied during the MR imaging data acquisition. FIG. 3A labels the "$k_{phase}$" and "$k_{read}$" k-space directions which correspond to the phase-encode gradient and readout gradient directions whose values are diagrammed in FIG. 2 on traces "$G_{phase}$" and "$G_{read}$" respectively. Remaining FIGS. 3B-3E use this same coordinate system as is used in FIG. 3A, but the axes are not labeled. In this k-space, lines containing the high MR signal lie in the k-space center.

Figure 3B:
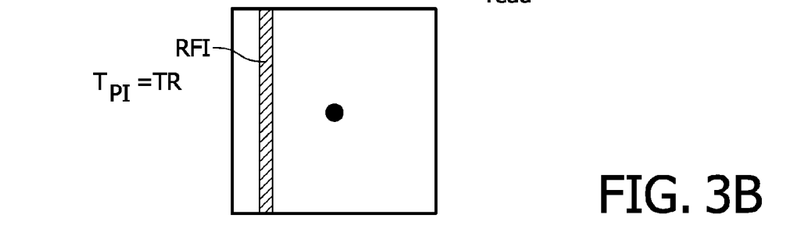

FIG. 3B illustrates one synchronization scheme, in which the MR sequence repetition period TR and the therapeutic pulse repetition period $T_{PR}$ are set equal.

It will be noted that this is the synchronization diagrammed in FIG. 2. In this case, all MR imaging data samples that overlap pulse intervals $T_{PI}$ will have the same $k_{phase}$ value. The corruption of MR imaging data samples due to therapeutic radiation-induced RFI is therefore all in one-half of the k-space, and along a single line of $k_{phase}$ values. This synchronization simplifies computation of non-measured/estimated MR imaging data sample values for insertion in place of the corrupted data. For a real object, k-space shows Hermitian k-space symmetry. This means there is redundancy in the data, which can be used to replace the corrupted ones by measured ones, using some small additional phase correction. Such approaches are known as partial Fourier reconstruction. The phase correction necessary can be obtained from the uncorrupted central data. This half Fourier approach is optionally further used to skip the acquisition of parts of the data. In this way only parts of the echo are acquired in the time domain (partial echo sampling), which reduces the effective data sampling period, so as to relax timing constraints of the source gating.

Figure 3C:
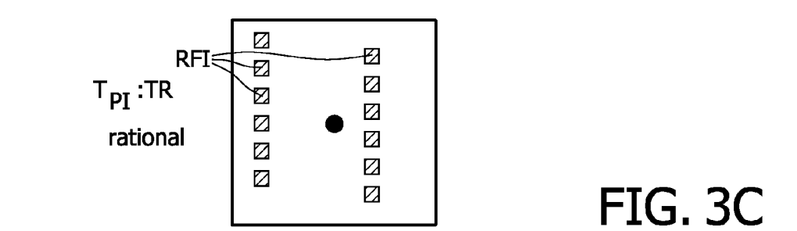

With reference to FIG. 3C, if both the MR and radiation therapy subsystems operate with a fixed but different repetition frequency, where the MR repetition time TR and the therapeutic radiation pulse repetition time $T_{PR}$ define a rational ratio, alternating k-space corruption can be obtained as shown in FIG. 3C. This means each second k-space line is corrupted, but in a different half of k-space. This synchronization also facilitates insertion of non-measured or estimated MR imaging data sample values computed using half Fourier techniques. In this synchronization, however, the phase correction is obtained from a preparatory MR scan, for example from the reference images stored in the reference images memory 70 or by sampling some acquired low-resolution profiles when the radiation therapy subsystem is not active.

Figure 3D:
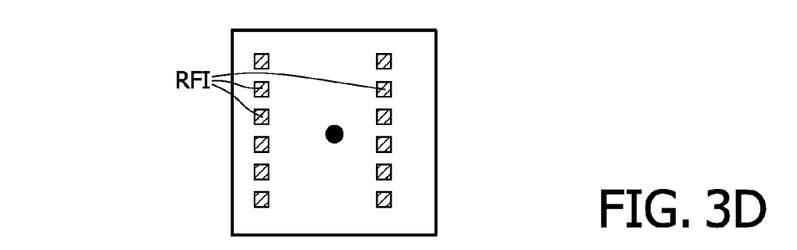

With reference to FIG. 3D, a synchronization scheme is employed in which each second line does not overlap any pulse intervals $T_{PI}$ and hence is uncorrupted. If the corrupted samples are omitted, then the dataset used for reconstruction is undersampled in a fashion similar to undersampling used in SENSE-type imaging approaches. Thus, if the one or more radio frequency coils 16 include a plurality of coils with different a priori known coil sensitivity profiles 52, then the redundancy in these data acquired by different coils can be used for correction. The missing data problem is similar to the undersampling problem known in parallel imaging like SENSE, and accordingly SENSE-type reconstruction algorithms can be used to compensate for the corrupted data using the coil sensitivity information. Use of a local k space estimation scheme (see, e.g., Griswold et al., Magn Reson Med vol. 47, pp. 1202-10 (2002)) is also contemplated to accommodate the sampling pattern shown in FIG. 3C without using the Hermitian symmetry approach. On the other hand, it is also contemplated to employ a synchronization scheme in which only each second line in k-space (or other multiples) is corrupted and the remaining lines are not corrupted. In this case sampling for corrupted k-space lines can be omitted entirely. The resulting data structure sampled is identical to a classical SENSE sub-sampling in which every other phase-encode line is omitted, and the under-sampled dataset can be reconstructed using conventional SENSE reconstruction.

Figure 3E:
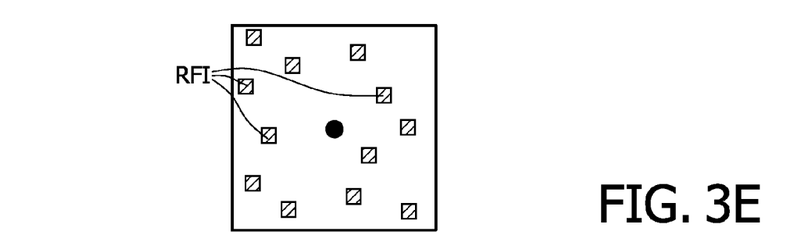

With reference to FIG. 3E, in other synchronization schemes by using appropriate ratios for the repetitions rates of the MR and radiation therapy subsystems, one can achieve a more stochastic signal corruption pattern in k-space. The synchronization can be optimised to ensure that the central k-space region is not corrupted. Such a dataset can be reconstructed using iterative schemes employing the iterative update processor 50. In the first iteration, image reconstruction is performed with all the corrupted data zero-filled or replaced by neighbourhood-average values. This gives rise to an image that shows artefacts, which are iteratively reduced using appropriate linear or nonlinear filtering in the spatial domain followed by projection of the image back into k-space so as to give better estimates for the corrupted data.

More generally, the reconstruction processor 44 can reconstruct the dataset without measured MR imaging data samples acquired during acquisition times that overlap pulse intervals to generate a reconstructed MR image using a generic optimization algorithm which solves the following equation:

$$\|F\rho - s\|_{L2} < T_{th} \quad (1)$$

under the constraint $$\min\|\psi\rho\|_{L1} \quad (2),$$

where $T_{th}$ is an error threshold. Equation (1) is the classical reconstruction problem using an L2 norm, where F denotes the Fourier operator or encoding matrix, $\rho$ the image to be reconstructed and s the measured samples in k-space. The constraints formulated in Equation (2) introduce a non-linearity via the operator $\psi$, which denotes for example the finite difference transform. The L1 norm of the finite difference transform is also known as the total variation. This set of Equations (1), (2) is solved iteratively using convex optimization. This is identical to compressed sensing as described in Candes et al., IEEE Tran. Info. Theo. vol. 52, pp. 489-509 (2006) and Donoho, IEEE Tran. Info. Theo. vol. 52, pp. 1209-1306 (2006), suggesting that by using nonlinear reconstruction algorithms, an accurate signal reconstruction can be obtained from a number of samples lower than that indicated by the Nyquist limit. This approach is facilitated by sampling which is equivalent to a random distribution of missing or corrupted data points in k-space.

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof. In the claims, any reference signs placed between parentheses shall not be construed as limiting the claim. The word "comprising" does not exclude the presence of elements or steps other than those listed in a claim. The word "a" or "an" preceding an element does not exclude the presence of a plurality of such elements. The disclosed method can be implemented by means of hardware comprising several distinct elements, and by means of a suitably programmed computer. In the system claims enumerating several means, several of these means can be embodied by one and the same item of computer readable software or hardware. The mere fact that certain measures are recited in mutually different dependent claims does not indicate that a combination of these measures cannot be used to advantage.

The invention claimed is:

1. A radiation therapy method comprising:
performing radiation therapy by applying a pulsed beam of ionizing radiation to a region of a subject during pulse intervals;
acquiring a dataset of magnetic resonance (MR) imaging data samples from the region of the subject over one or more MR sampling intervals that are longer than the pulse intervals, the one or more MR sampling intervals overlapping at least some of the pulse intervals; and
reconstructing the dataset without the measured MR imaging data samples acquired during acquisition times that overlap pulse intervals to generate a reconstructed MR image.

2. The radiation therapy method as set forth in claim 1, further comprising:
inserting non-measured or estimated MR imaging data sample values into the dataset for those MR imaging data samples whose acquisition times overlap pulse intervals; the reconstructing comprising reconstructing the dataset with the inserted non-measured or estimated MR imaging data sample values to generate the reconstructed MR image.

3. The radiation therapy method as set forth in claim 2, further comprising:
generating a simulated dataset of MR imaging data samples from the reconstructed MR image;
updating the non-measured or estimated MR imaging data sample values based on the generated simulated dataset; and
reconstructing the dataset with the updated, inserted non-measured or estimated MR imaging data sample values to generate an improved reconstructed MR image.

4. The radiation therapy method as set forth in claim 2, further comprising:
constructing the non-measured or estimated MR imaging data sample values from acquired MR imaging data samples whose acquisition times do not overlap pulse intervals, based on a Hermitian k-space symmetry.

5. The radiation therapy method as set forth in claim 4, further comprising:
selecting at least one of (i) a repetition time of the acquiring and (ii) a pulse repetition time interval separating the pulse intervals such that the MR imaging data samples whose acquisition times overlap pulse intervals all lie in one half of k-space.

6. The radiation therapy method as set forth in claim 4, further comprising:
selecting
(i) a pulse repetition time interval separating the pulse intervals, and
(ii) a repetition time of the acquiring,
such that the repetition time of the acquiring and the pulse repetition time interval define a rational ratio.

7. The radiation therapy method as set forth in claim 1, wherein the acquiring employs a plurality of radio frequency receive coils having different coil sensitivities, and the reconstruction comprises:
reconstructing the dataset without those MR imaging data samples whose acquisition times overlap pulse intervals, the said dataset being undersampled; and
compensating for undersampling based on additional information provided by sensitivities of the plurality of radio frequency receive coils.

8. The radiation therapy method as set forth in claim 1, further comprising:
detuning a radio frequency receive coil during the pulse intervals.

9. The radiation therapy method as set forth in claim 1, further comprising:
identifying a subject motion based on the reconstructed MR image; and
adjusting the applying of the pulsed beam of ionizing radiation performed subsequent to the identifying to adapt the radiation therapy to accommodate the identified subject motion.

10. The radiation therapy method as set forth in claim 1, wherein the pulsed beam of ionizing radiation comprises: gamma particles, alpha particles, beta particles or x-ray photons.

11. The radiation therapy method as set forth in claim 1, wherein the pulsed beam of ionizing radiation interacts with and damages tumor tissue.

12. A radiation therapy system comprising:
a radiation therapy subsystem configured to perform radiation therapy by applying a pulsed beam of ionizing radiation to a region of a subject at pulse intervals;
a magnetic resonance (MR) imaging subsystem configured to acquire a dataset of MR imaging data samples from the region of the subject over one or more MR sampling intervals that are longer than the pulse intervals, the one or more MR sampling intervals overlapping at least some of the pulse intervals;
a synchronizer configured to identify MR imaging data samples of the dataset whose acquisition times overlap pulse intervals; and
a reconstruction processor configured to reconstruct the dataset without the measured values for the MR imaging data samples identified as having acquisition times overlapping pulse intervals to generate a reconstructed MR image.

13. The radiation therapy system as set forth in claim 12, wherein the synchronizer is further configured to select at least one of (i) a repetition time of the dataset acquisition and (ii) a pulse repetition time interval separating the pulse intervals in order to define which MR imaging data samples of the dataset have acquisition times overlapping pulse intervals.

14. The radiation therapy system as set forth in claim 12, wherein the reconstruction processor is configured to insert non-measured or estimated MR imaging data sample values into the dataset for the MR imaging data samples identified as having acquisition times overlapping pulse intervals, the reconstruction processor being configured to reconstruct the dataset with the inserted non-measured or estimated MR imaging data sample values to generate the reconstructed MR image.

15. The radiation therapy system as set forth in claim 12, wherein the MR imaging subsystem comprises:
a plurality of radio frequency receive coils having different coil sensitivities, the reconstruction processor configured to (i) reconstruct the dataset without the MR imaging data samples identified as having acquisition times overlapping pulse intervals, said dataset being undersampled, and (ii) compensate for the undersampling based on additional information provided by the plurality of radio frequency receive coils having the different coil sensitivities.

16. The radiation therapy system as set forth in claim 12, wherein the pulsed beam of ionizing radiation comprises: gamma particles, alpha particles, beta particles or x-ray photons.

17. The radiation therapy system as set forth in claim 12, wherein the pulsed beam of ionizing radiation interacts with and damages tumor tissue.

* * * * *